Feb. 26, 1974 W. A. WARRINER Plant Pat. 3,492
ROSE PLANT
Filed Oct. 4, 1972
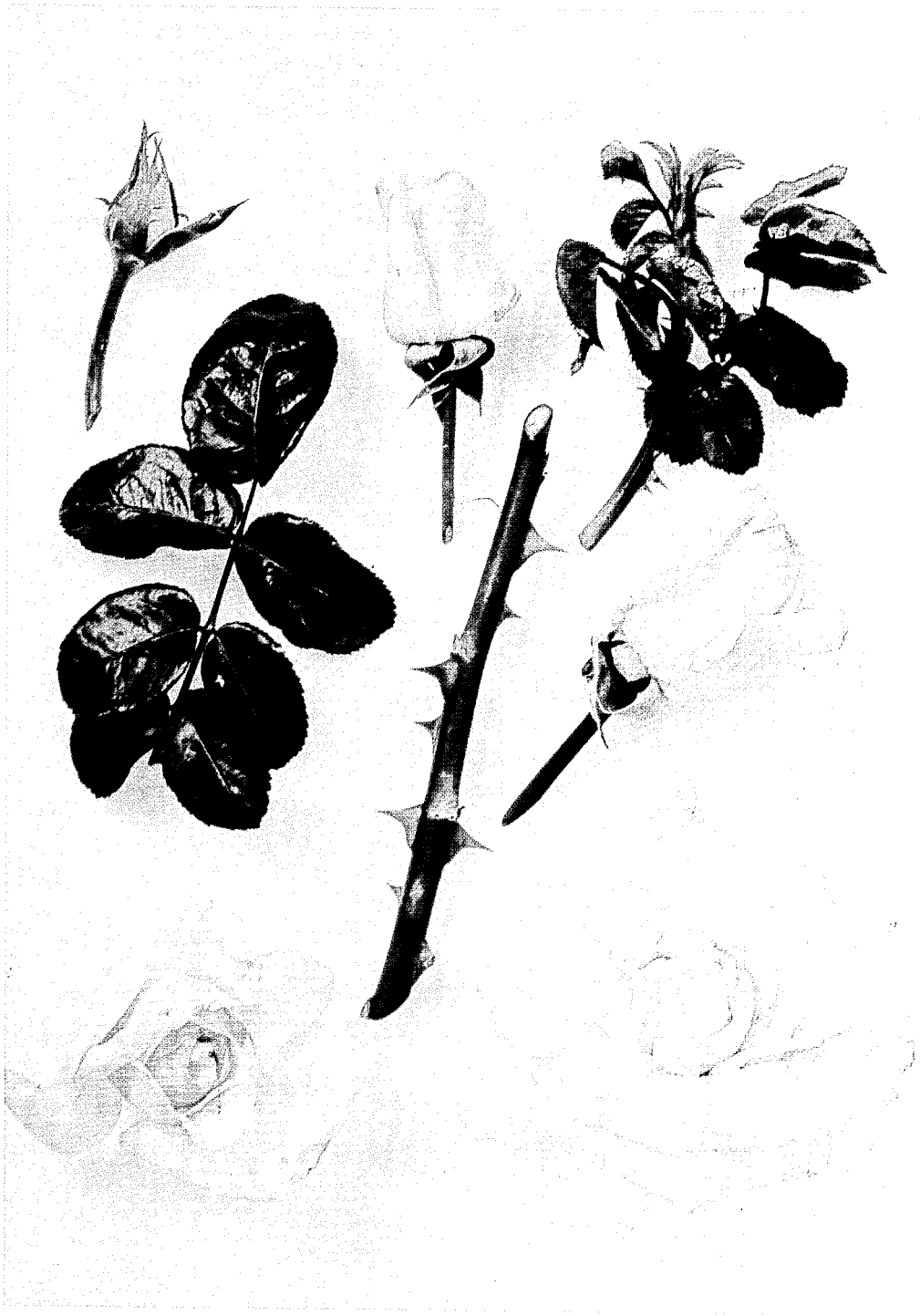

United States Patent Office

Plant Pat. 3,492
Patented Feb. 26, 1974

3,492
ROSE PLANT

William A. Warriner, Tustin, Calif., assignor to Jackson & Perkins Company, Medford, Oreg.

Filed Oct. 4, 1972, Ser. No. 294,993
Int. Cl. A01h 5/00
U.S. Cl. Plt.—18 1 Claim The present invention relates to a new and distinct variety of rose plant of the hybrid tea class which was originated by me by crossing the variety South Seas, U.S. Plt. Pat. 2,184, with the variety Peace, U.S. Plt. Pat. 591.

The primary objective of this breeding was to produce a new rose variety combining the good characteristics of both parent varieties with a flower color preferably pink. This objective was substantially achieved along with other desirable improvements as evidenced by the following unique combination of characteristics which are outstanding in the new variety and which distinguish it from its parents as well as from all other varieties of which I am aware:

(1) A vigorous, upright habit of growth.
(2) An abundance of dark green, glossy foliage.
(3) Flower color changing from Camellia rose in the tight bud stage to lighter tint of Camellia rose in the open flower, with the reverse of the petals being Dawn pink.
(4) Very little fragrance.

Asexual reproduction of this new variety by budding, as performed at Wasco, Calif., shows that the foregoing characteristics and distinctions come true to form and are established and transmitted through succeeding propagations.

The accompanying drawing shows typical specimens of the vegetative growth and flowers of this new variety in different stages of development, depicted in color as nearly true as it is reasonably possible to make the same in a color illustration of this character.

The following is a detailed description of my new rose variety with color terminology in accordance with Wilson's Horticultural Color Chart, except where ordinary dictionary significance of color is indicated.

*Seed parent* ---- South Seas (U.S. Plt. Pat. 2,184).
*Pollen parent* --- Peace (U.S. Plt. Pat. 591).

Classification:
*Botanic.*—Rosa Hybrid.
*Commercial.*—Hybrid Tea.

FLOWER

Observations were made at Irvine, Calif., in early September in the afternoon.

Blooming habit: Recurrent—continuous.
Bud:
*Size.*—One inch to 1¼ inches when petals start to unfurl.
*Form.*—Pointed, ovoid.
*Color.*—When sepals first divide—Camellia Rose (622/1). When half blown; inside of petals—Camellia Rose (622/3). Reverse of petals—Dawn Pink (523/2).
*Sepals.*—Color: Outer surface—Scheeles Green (860/1). Inner surface—same color but covered with white tomentum. Three appendaged sepals lightly appendaged. Two unappendaged sepals, hairy edge.
*Receptacle.*—Color: Scheeles green (860/1). Shape: Funnel. Size: Large. Surface: Smooth.

*Peduncle.*—Length: Short. Surface: Glossy with few prickles. Color: Scheeles green (860/1). Strength: Stiff, erect.
*Opening.*—Outer petals curl slightly as they fold open.
Bloom:
*Size.*—Large. Average size when fully expanded, 4½ to 5 inches.
*Borne.*—Singly, occasionally several together.
*Stems.*—Long, strong.
*Form.*—When first open, high center. Center petals in irregular formation. Permanence—outer petal edges slightly curled.
*Petalage.*—Number of petals under normal conditions 40 to 45.
*Color.*—Center of flower: Upper side of petals Camellia Rose (622/3). Reverse side of petals Dawn Pink (523/2). Outer petals: Upper side of petals Camellia Rose (622/3). Reverse side of petals Dawn Pink (523/2). Base of petals: Small area near Empire yellow (603/1). General tonality from a distance deeper than Camellia Rose because of the Dawn Pink on reverse of petals. No variegations.
*Discoloration.*—By third day very slightly lighter.
*Fragrance.*—None.
Petals:
*Texture.*—Thick.
*Surface.*—Inside—satiny. Reverse—satiny.
*Shape.*—Nearly deltoid when held flat.
*Form.*—Edges slightly curled.
*Arrangement.*—Informal.
*Petaloids in center.*—Few, large.
*Persistence.*—Drop off cleanly.
*Lastingness.*—On the plant—long. As cut flower—long.
Reproductive Parts:
*Stamens, anthers.*—Medium. Color—yellow. Arrangement—regular around styles.
*Stamens, filaments (threads).*—Irregular. Color—pink.
*Pollen.*—Gold yellow.
*Styles.*—Loosely separated, of uneven lengths.
*Stigmas.*—Color—white.
*Ovaries.*—All enclosed in calyx.

PLANT

Form: Bush.
Growth: Very vigorous.
Foliage: Number of leaflets on normal mid-stem leaves 5, occasionally 7.
*Size.*—Very large.
*Quantity.*—Normal.
*Color.*—New foliage: Garnet brown (00918/3)—Old foliage: Upper side—Parsley green (00962/1). Lower side—Spinach green (0960/3).
Leaflets:
*Shape.*—Oval.
*Texture.*—Glossy. Under side smooth. Ribs and veins ordinary.
*Edge.*—Serrated.
*Serration.*—Single, small.
*Petiole (rachis).*—Color: Upper side reddish. Lower side—green. Underside—prickles and stipitate glands.
*Stipules.*—Long. Edges very glandular.
*Disease resistance.*—Normal resistance to mildew at Irvine, Calif.
Wood:
*New wood.*—Color—light green. Bark—smooth.
*Old wood.*—Color—green. Bank—smooth.

Prickles:

*Quantity.*—On main stalks—ordinary. On laterals—ordinary.

*Form.*—Broad based, hooked downward.

*Color.*—When young—red near base, green on tips.

*Position.*—Irregular.

Small prickles:

*Quantity.*—On main stalks—none. On laterals—none.

I claim:

1. A new and distinct variety of rose plant of the hybrid tea class, substantially as herein shown and described, characterized particularly as to novelty by the unique combination of its dark, glossy foliage; vigorous, upright habit of growth; Camellia rose flower color with the reverse of the petals being Dawn pink.

No references cited.

ROBERT E. BAGWILL, Primary Examiner